United States Patent
Diaz Sanchez et al.

(10) Patent No.: US 9,826,886 B2
(45) Date of Patent: Nov. 28, 2017

(54) TWO-WAY PHOTODYNAMIC THERAPY STEREO COLPOSCOPE FOR DIAGNOSING AND TREATING DISEASES OF THE FEMALE GENITAL TRACT

(76) Inventors: Joel Gerardo Diaz Sanchez, Colonia San Pedro de Los Pinos (MX); Jose Gerardo Zertuche Zuani, Colonia Roma (MX)

( * ) Notice: Subject to any disclaimer, the term of this patent is extended or adjusted under 35 U.S.C. 154(b) by 271 days.

(21) Appl. No.: 14/111,356

(22) PCT Filed: Apr. 15, 2011

(86) PCT No.: PCT/MX2011/000044
§ 371 (c)(1),
(2), (4) Date: Oct. 11, 2013

(87) PCT Pub. No.: WO2012/141563
PCT Pub. Date: Oct. 18, 2012

(65) Prior Publication Data
US 2014/0031702 A1    Jan. 30, 2014

(51) Int. Cl.
*A61N 5/06* (2006.01)
*A61B 5/00* (2006.01)
(Continued)

(52) U.S. Cl.
CPC ...... *A61B 1/00087* (2013.01); *A61B 1/00186* (2013.01); *A61B 1/00193* (2013.01);
(Continued)

(58) Field of Classification Search
CPC .................................................. A61N 5/062
(Continued)

(56) References Cited

U.S. PATENT DOCUMENTS 1,780,600 A  *  11/1930  Pullwitt .................. A61N 1/403
                                                       313/243
3,373,747 A  *  3/1968   Tapper ............... A61N 1/36014
                                                       30/34.2
(Continued)

FOREIGN PATENT DOCUMENTS

EP           1 700 561 A1    9/2006
WO      WO-01/72216 A2     10/2001
WO   WO-2005/039403 A1     5/2005

OTHER PUBLICATIONS

"Master Appliance," "The Master Violet Ray," Early American Energy Medicine, (published Feb. 1, 2002 at http://www.mcmillinmedia.com/eaem/master1/mastcont.html).*

(Continued)

*Primary Examiner* — Patricia Park
(74) *Attorney, Agent, or Firm* — Harness, Dickey & Pierce, P.L.C.

(57) ABSTRACT

A stereo colposcope having variable linearity filter systems for both the excitation step and the suppression step, and can be used universally with any fluorescent compound or drug, as is the case of photodynamic diagnosis (PDD). The colposcope is a two-way colposcope because the treatment can be administered by an optical system or by a light-producing radio-frequency electrical current with a diathermic effect which facilitates photodynamic treatment. The colposcope produces ozone, which has an antiseptic effect when applied to the genital tract. A monitor provides for three-dimensional viewing through the use of two video cameras with the DLP (Digital Light Processing) and HDTV (High Definition Television) systems with the use of active lenses.

8 Claims, 2 Drawing Sheets

(51) Int. Cl.
*A61B 1/00* (2006.01)
*A61B 1/303* (2006.01)
*G01N 21/64* (2006.01)
*A61B 1/05* (2006.01)
*A61B 1/06* (2006.01)
*A61B 1/07* (2006.01)
*A61N 1/00* (2006.01)
*A61B 1/04* (2006.01)

(52) U.S. Cl.
CPC ............ *A61B 1/043* (2013.01); *A61B 1/05* (2013.01); *A61B 1/0646* (2013.01); *A61B 1/0676* (2013.01); *A61B 1/07* (2013.01); *A61B 1/303* (2013.01); *A61B 5/0084* (2013.01); *A61B 5/4337* (2013.01); *A61B 5/4836* (2013.01); *A61N 1/00* (2013.01); *A61N 5/062* (2013.01); *A61N 5/0603* (2013.01); *G01N 21/6456* (2013.01); *G01N 2021/6419* (2013.01); *G01N 2021/6421* (2013.01)

(58) Field of Classification Search
USPC .......................................... 604/20
See application file for complete search history.

(56) References Cited

U.S. PATENT DOCUMENTS

| | | | | |
|---|---|---|---|---|
| 4,222,653 A * | 9/1980 | Beiser | ............... | G02B 27/2207 396/324 |
| 6,389,312 B1 * | 5/2002 | Duckert | ............... | A61B 5/1106 600/546 |
| 2002/0001202 A1 * | 1/2002 | Williams | ............... | A61B 17/02 362/572 |
| 2003/0002028 A1 * | 1/2003 | Rice | ................... | G01N 21/4795 356/39 |
| 2004/0162489 A1 * | 8/2004 | Richards-Kortum | | A61B 5/0071 600/473 |
| 2005/0033127 A1 * | 2/2005 | Ciurczak | ............ | A61B 5/14532 600/316 |
| 2005/0280631 A1 * | 12/2005 | Wong | ...................... | G02B 6/06 345/158 |
| 2007/0106172 A1 * | 5/2007 | Abreu | .................. | A61B 5/0002 600/549 |
| 2007/0167838 A1 | 7/2007 | Hubble et al. | | |
| 2007/0191675 A1 * | 8/2007 | Diaz Sanchez | ...... | A61B 1/0646 600/105 |
| 2008/0147053 A1 * | 6/2008 | Kang | .................. | A61B 5/0071 606/9 |
| 2009/0240138 A1 * | 9/2009 | Yi | ...................... | G01N 21/4795 600/425 |
| 2009/0266999 A1 * | 10/2009 | Krattiger | ............ | A61B 1/00096 250/459.1 |
| 2010/0145416 A1 * | 6/2010 | Kang | .................. | A61B 5/0059 607/89 |
| 2010/0302235 A1 * | 12/2010 | Darshan | .................... | G06T 5/50 345/419 |

OTHER PUBLICATIONS

"The Turn of the Century Electrotherapy Museum Violet Ray Misconceptions Article," ( published at Nov. 2, 2004, http://www.electrotherapymuseum.com/Articles/VioletRayMisconceptions.htm ).*

International Search Report for PCT/MX2011/000044, dated Dec. 27, 2011; ISA/ES.

* cited by examiner

TWO-WAY PHOTODYNAMIC THERAPY STEREO COLPOSCOPE FOR DIAGNOSING AND TREATING DISEASES OF THE FEMALE GENITAL TRACT

CROSS-REFERENCE TO RELATED APPLICATIONS

This application is a 371 U.S. National Stage of International Application No. PCT/MX2011/000044, filed Apr. 15, 2011, the disclosure of which is herein incorporated by reference in its entirety.

TECHNICAL FIELD

I. Medical field: a) Medical Imaging, b) Phototherapy, c) Electrotherapy
II. Technology field: a) Surgical microscopes, b) Stereomicroscopes, c) Medicine-applied Optics, d) Medical Instruments and Equipment

STATE OF THE ART

Since the second half of the nineteenth century, photonics and electronics technologies have led to a plethora of scientific and technological developments for medical diagnosis and treatment, resulting in new devices with which research and a better understanding about the interaction of medical instrumentation, optics and electronics with biological tissues belonging to the field of immunohistochemistry and pathology have been conducted, targeting, as in our case, the study, diagnosis and treatment of female genital tract.

As sexually transmitted diseases are currently considered emerging, there has been accordingly an increasing demand to solve women's genital tract diseases, leading to new medical device development in the last twenty years, both for diagnosis and medical treatment; however, these new methods have various disadvantages, including the high economic cost with their use, as in developing countries is almost impossible to reach the required technological level.

Examples of these high-tech diagnosis methods include fluorescence spectroscopy and optical coherence tomography and many others.

Colposcopy has been a method which is somehow economical for sexually transmitted disease diagnosis as it is a method for direct visualization allowing a quick observation of disease signs, and especially human papillomavirus-produced neoplasms.

The instrument used to perform a gynecological examination colposcopy in the genital tract is commonly called a colposcope which increases the image size, that is, a stereoscopic microscope taking advantage of vision with both eyes facing three-dimensional images by two separate eyepieces, similar to an angle formed between the eye visual axes (7 to 12 degrees) providing two different images, one for each eye, and a three-dimensional perception, this being indispensable to perform several manual operations implemented in the genital tract. In the light of above, the so-called colposcope correct name is "stereocolposcope" as in present case.

The stereocolposcope was invented in Germany in 1925 by Dr. Hans Hinselmann who dissatisfied with the used scanning means of that time and intending to discover the initial forms of female genital tract diseases, combined a powerful light source with a stereoscopic zoom system for observation. The stereocolposcope has virtually remained unchanged since 1925 when it was invented.

The authors of this paper previously invented the "actinic light colposcope" with WIPO International Publication number: WO 2005/039403 A1, for early diagnosis of lesions caused by human *papilloma* virus, known as neoplasms which are cervical cancer precursors.

The stereocolposcopes are currently used in routine gynecological examination for purposes of diagnosis, however, any of these stereocolposcopes having simultaneous functions of diagnosis and treatment is not available. The new colposcope claimed herein as "two-way photodynamic therapy stereocolposcope" not only further improves the sensitivity and specificity in sexually transmitted disease diagnosis, as it further combines medical treatment with diagnosis through optical and electronic devices for photodynamic therapy application allowing a successful treatment of various genital tract diseases, being also highly effective in treating precursor neoplasms applied to cervical cancer.

BACKGROUND OF THE INVENTION

For a proper understanding of the operation and benefits of this new apparatus, the concepts required thereto, including the related problems, are firstly described.

Sexually transmitted diseases (STD) are those which are transmitted during sexual intercourse being usually asymptomatic and where any sexually active person is at risk of acquiring them.

There are several types of pathogens that produce them, including: mycoses producing fungi, bacteria, protozoa and viruses.

We found the combination of multiple pathogens in most of infected cases. Vaginosis and cervicitis remain as the most common worldwide, high economic impact, female genital tract disorders in reproductive-age women.

The human *papilloma* virus in these diseases requires special attention because it is the cause of neoplasms, which are the cervical cancer precursor lesions.

The virus genus *Papilloma* is too long, being DNA viruses that infect many animal species, including humans. There are over 100 types of these known as Human *Papilloma* Virus (HVP).

Interest in these viruses has increased gradually since 1970, when they had firstly an attributed role in cervical cancer etiology.

Cervical cancer is a common type of cancer in women, being a change in the cervix epithelial tissue cells and also in vaginal walls and vulva. These cells are initially normal and they then gradually become precancerous. Tissues undergo changes before cancer cells are present in the cervix, and abnormal cells called koilocytes begin to appear, this process known as dysplasia or cervical intraepithelial neoplasia (CIN).

There are over 30 types of HVP virus having the ability to infect the lower female genital tract; benign virus called "low risk" and other oncogenic called "high risk" are within these types. The high-risk viral type in America has been the HPV 16 Asian-American variety in about 50% of cases.

Cervical cancer is one of the most common cancers in women. More than 500,000 cases per year are estimated worldwide. About 80% of these occur in developing countries. The high event incidence reflects poor programs in early disease detection, and a lack of new medical devices for diagnosis and treatment thereof.

Phototherapy is the action of light on biological tissues for therapeutic purposes. A phenomenon of the interaction of light with a dye called acridine was observed in 1900 which was also used in histological staining techniques, noticing that this dye when ingested by a living organism called paramecium caused its death when exposed to light.

The first oncology use was in 1903 when another histology dye called eosin together with light was used and applied to a skin cancer type with curing purposes.

Hematoporphyrins started their use in cancer research in 1914, these dyes and fluorochromes being called photosensitizers. Many attempts were then flawed due to impurities present in these photosensitizers.

Nowadays it is said that photodynamic therapy (PTD) is a therapeutic method based on biological material photo-oxidation induced by incubating a precursor for a photosensitizing agent, which is selectively deposited within target cells or blank cells, in order to destroy selectively damaged or altered cells in their nuclear structure.

Damage is due to high oxygen molecule reactions producing oxygen intermediates such as singlet oxygen, the main death cause of tumor cells.

In 1969, Richard Lipson and Gregorie observed that hematoporphyrins derivatives (HPD) could be used as photosensitizing agents on tumor cells as these agents have a mitochondrial specificity mechanism, being deposited in neoplastic tissue which when lighted up, a selective destroy is achieved without any damage to adjacent healthy tissues.

Besides therapeutic applications, this treatment is also used as a diagnosis method currently known as photodynamic diagnosis (PDD), since the photosensitizer emitted fluorescence may be detected by tumor tissues notably distinguished from healthy tissues.

Most commonly used photosensitizing agents are 5-aminolevulinic acid (ALA), methyl aminolevulinate (MAL) and hexaminolevulinate (RAL). ALA is considered the first step in the metabolic process of hemo-group formation, then it may actually not be a photosensitizing agent by itself, however, its structure is crucial as a protoporphyrin IX (PpIX) precursor which is indeed a photosensitizing agent and when under normal conditions, ALA is firmly controlled by a feedback direct mechanism through Ala synthetase present in hemo-cell nuclei. When ALA is intracellularly activated PpIX production is increased, which in turn becomes into hemo through a ferrochelatase adding iron ions to PpIX. Such photosensitizing agents may be administered by enteral, parenteral and topical route.

In the nineteenth century during 1875, Jacques-Arsene d'Arsonval who was a laboratory apprentice of the famous physiologist Claude Bernal, began experimenting with high-frequency electrical current therapeutic application applied to a number of diseases; at that time (1892) d'Arsonval met Nikola Tesla and both shared views and knowledge in harmony. From these experiments a new medical device emerged which could generate radio frequency waves like transmission waves of amplitude modulation in current commercial band, and these were applied to human body using an applicator consisting of a vacuum glass tube, capable of safely transmitting electric and photon current to human body in the form of electric arc but effective for curing various diseases, especially those caused by pathogenic microorganisms, and which due to ozone and light occurring around the tube, the ozone may kill these pathogens.

Frederick Finch Strong was the physician who invented this glass vacuum tube in 1896, which was further used in the telegraph and radio telephone industry of that era when the first bulbs were made with this principle.

d'Arsonval's apparatus or machine is built with a Ruhmkorff induction coil, Leiden bottles (now known as capacitors), lighters, a high frequency d'Arsonval coil, an Oudin resonator whereby the end cable thereof is connected to the applicator electrode, which is the Strong Finch vacuum glass tube.

Since early in twentieth century to early 50's, thousands of these devices were built within the United States of America, these devices being known as "violet ray machine." These devices were out from trade in the U.S. about 1954 due to chemical and pharmaceutical industry pressure and also due to medical abuse thereon. FDA has currently approved again the use thereof in America. However, in countries such as Germany, Russia, Ukraine and others in Europe, the benefits of the violet ray machine—known in Europe as "d'Arsonval machine"—are still under research.

Nowadays, the electro-photonic light arc occurring within a Finch Strong tube may be of any color, and this is why we are the first authors worldwide in introducing these knowledge and techniques within the field of photodynamic therapy.

Within the application of these rays as part of our Stereocolposcope, we have as innovation in the female genital tract therapy:

A).—When producing a powerful electric and light arc, we may cause that the photodynamic therapy photosensitizer reacts more effectively in singlet oxygen production within neoplastic or cancerous cells, thus eliminating them.

B).—In producing a photoelectric arc, a diathermic effect innocuous heat also favors the photosensitizer reaction.

C).—As stated in previous paragraph, the photoelectric arc color may be located in the intended visible spectral frequency so that its use is universal, i.e., we may apply it to any current or future photosensitizer available in market for photodynamic therapy as each laboratory or brand thereof reacts at different spectral wavelength.

D.)—In photoelectric arc production, a large amount of ozone lethal for several pathogens is formed thus fighting them within the female genital tract.

The commonly used method for light energy application and transportation in photodynamic therapy is by using optical fibers. An optical fiber is a tube wherein light is transmitted through its ends, this physical phenomenon known as refraction. This knowledge is not new since physicist John Tyndall in England demonstrated in nineteenth century that water from a tank comprising an internal light source, when expelled through a hole, the water jet led light to the receiving vessel.

Image transmission through tubes was made by radio experimenter Clarence Hansel and television pioneer John Logie Baird in 1920; the first uses of these tubes were for medical examination purposes; the first flexible gastroscope was released years later in 1956.

Nowadays, several optical fiber types are available in market, whether in fiber bundles or mono-cable, which are widely used in optical field for multiple purposes depending on their characteristics.

The latest optical fibers for medical applications, given their high light flux conduction, flexibility and durability, contain fluorinate, ethylene and propylene resins (FEP), which are under experimentation in this field in Australia.

PROBLEM

Infectious etiology female genital tract diseases including the lesions caused by human papillomavirus (HPV), which are known as cervical intraepithelial neoplasm (CIN) are often undiagnosed and not easily treated. This is due to a lack of equipment and tests in doctor's office setting easing the diagnosis of said diseases causing that the gynecologist turns to laboratory tests with wide margin of error, or to the use of sophisticated and high cost equipment, for example, those of spectroscopy and optical coherence tomography requiring a long training and only available in industrialized countries but not in developing countries due to a number of factors. This results in patients suffering of long waiting times and multiple doctor visits.

As to currently used therapy techniques for cervical cancer and especially for neoplasms (CIN), their use leads to cervical tissue loss and leaves lasting remnants for life, sometimes producing uterine or cervical synechiae which are scars in the uterus or cervix cavity where tissues adhere by fibrous membranes, causing pelvic infections, or the formed fibrous tissue may potentially cause infertility by preventing the passage of sperm or endometriosis by impeding menstrual outflow. It may also cause the so-called "incompetent cervix", i.e., cervical muscle fibers providing firmness thereto and used to support the baby weight during the nine pregnancy months when cut or injured, lose their strength when a woman becomes pregnant which leads to premature membrane rupture (MPR) causing immature baby deliveries and having several consequences such as newborn retinopathy which is virtually permanent blindness in the product, or even death thereof.

Current therapies may also include human papillomavirus vaccination. Vaccines directed to disease treatment are still in experimental phase and prophylactic vaccines such as tetravalent vaccine targeting HPV-16, HPV-18, HPV-11 and HPV-6 viral types, limited to application in women, is applied in women ranging 9 to 27 years old provided they have had no contact with this virus.

Currently there is significant controversy for their use in the U.S. and Europe. The other vaccine is targeted to HPV-16 and HPV-18 *papilloma* virus types with similar limitations. Costs of both vaccines are high for both government administrations and individuals, the biggest problem being that real immunization time is not yet known in each of the viral types providing protection.

OBJECTIVE OF PRESENT INVENTION

In order to solve above problems, the creation of this new invention: "Two-way photodynamic therapy stereocolposcope for diagnosing and treating diseases of the female genital tract" was envisaged, which performs an early diagnosis and provides timely treatment of female genital tract infectious diseases, as well as neoplasms caused by human *papilloma* virus that cause cervical cancer when patient is scanned, i.e., it is a dual function "Watch and treat" instrument.

Costly studies or long-term processes and procedures are prevented with the new stereocolposcope thus providing highly reliable results regarding detection and treatment of sexually transmitted diseases and neoplasms caused by human *papilloma* virus (HPV) by applying the fluorescence phenomenon, photodynamic therapy and purifying-ozone production electrotherapy.

One of the main objectives in the application of the therapy of present invention consists of cervical tissue preservation without damage, due to its selective cellular action while just removing unwanted, malignant or infected cells within tissues.

As to human papillomavirus (HPV) elimination, a possibility of virus inactivation is present due to photodynamic therapy application, and this device becomes very promising within cervical cancer prevention programs.

The new stereocolposcope also works as a common stereocolposcope.

DETAILED DESCRIPTION OF THE APPARATUS

The invention and its systems described and detailed in this document basically form a stereocolposcope consisting of:

A variable linear type excitation filter system is present in the head lighting system, capable of choosing any light frequency range to generate a light beam to any fluorescent compound located at the female genital tract, these compounds may be: fluorophores, "in vivo" use fluorescent proteins of any color, or chemical dyes for fluorescence. This filter covers a range from 400 nanometers to 1080 nanometers, the light beam band capable of being selected every 20 nanometers.

In order to analyze the frequency emitted by fluorescent compounds and to eliminate wavelengths produced by the excitation light, two suppressor or barrier filters have been assembled on stereocolposcope head, one for each observation optical axis. These filters are also of variable linearity for accurately adjusting the emission beams issued from the compound to be reacted in the dyed female genital tract. These filters span a light spectrum from 400 to 700 nanometers, which is the visible light spectrum, and frequencies may be staggered every 20 nanometers.

Two diaphragms are also located on the head in order to match what is being observed and also for watching the depth of field, one diaphragm at each optical axis with manual aperture controller.

The three-dimensional observation in this novel stereocolposcope may be by direct observation through the eyepieces as usual in these devices, or by the novel way of having two high-resolution video cameras located on the head, each camera being located at each visual axis. The three-dimensional vision video system is: DLP (digital light processing) HDTV (high definition television) with the use of three-dimensional active lenses.

This photodynamic therapy stereocolposcope has been called "two-way" because it has two additional light housings for photodynamic therapy application in addition to the head-based lighting system.

A light source housing with focusable optical system is targeted to a medical grade optical fiber or to the novel low cost and high quality optical fiber made of ethylene and propylene fluorinate resin (FEP). Similarly to the head, a variable linearity filter is placed within the optical system also being capable of choosing any light frequency range for sending a light beam through the optical fiber to any compound or drug within the female genital tract for photodynamic therapy application, this filter spans a range from 400 nanometers to 700 nanometers, with a light beam band which may be chosen every 20 nanometers thus providing a virtually universal equipment application to any drug intended for photodynamic therapy.

A housing with d'Arsonval System (violet ray housing), is built with Ruhmkorff induction coil, Leiden bottles (now known as capacitors), lighters, a high frequency d'Arsonval coil, an Oudin resonator whereby the radio frequency emission end cable thereof is connected to the applicator electrode, which is the Strong Finch vacuum glass tube. The set of vacuum tubes is of vaginal type emitting different colors which span the visible light spectrum, for reacting in a universal way with any drug or compound for photodynamic therapy application, the Finch Strong vacuum glass tube further produces a diathermic effect useful in accelerating the compound reaction. Another function of this tube is an antiseptic effect ozone production in the diseased tissue surface which may kill the germs causing infection in the female genital tract mucosa.

It is worth to mention that several authors classify both, high frequency d'Arsonval coil and Oudin resonator, as Tesla coils.

It is important to show and to emphasize that the scope of this invention goes beyond current knowledge and diagnoses in the field of Colposcopy and also in the application of Photodynamic therapy, and this equipment is a strong tool for future innovations in diagnosis and treatments, opening a new gate in female genital tract disease clinical research. Set of Parts in the Two-Way Photodynamic Therapy Stereocolposcope for Diagnosis and Treatment of Female Genital Tract Diseases.

The new stereocolposcope comprises several parts structuring its systems. These are: mechanical, optical, and electronic parts, which structure 3 assemblies.

I.—Mechanical Assembly

This set is the frame or skeleton, comprising and supporting the optical and mechanical parts of the equipment:

Base and Support:

Comprised by a balanced steel disc providing stability to the equipment, four or six independent rotary wheels with a brake mechanism for equipment positioning, a vertical stainless steel tube and a horizontal support with a rotating joint for arm and head assembly and maneuvering; light housing and system power source electronics are located in the horizontal support above the base disc.

Arm:

A balanced mechanism which allows three-axis motion. Such motion provides the exact head location at different working heights and positions, giving the possibility to easily maneuver the equipment at the time of a gynecologic procedure.

Head:

The central and most important part of the equipment. In other words, this is truly the new stereocolposcope, housing the following components: focusing system with fine motion mechanism and optical system comprising two filter types, head variable linearity excitation filter and variable linearity suppressor filters. This is the stereocolposcope core where light energy transmission and modulation is carried out which allows cervix image monitoring with different amplifications directly through Galileo drum or through the two high-resolution digital television cameras located at the sides of said head transmitting the image to a monitor in the novel three-dimensional DLP HDTV system.

II.—Electronic Assembly:

A high-amperage "line isolator" power transformer providing the required volt/amperes for other electronic components without any component related with the apparatus power line is arranged, due to high safety reasons and since the equipment operates with radio frequency waves for light emission and ozone production. This apparatus works with 240-220 volt current lines (European), 110-120 v (American) and 90-100V (Japanese).

A power source to supply metal halide light bulbs, a power source for Xenon light bulbs and the respective ballast for lighting thereof.

A pair of metal halide bulbs is placed in the head, having detectors for inner temperature monitoring and regulation, connected to printed circuits controlling the temperature and regulating the fan blade revolutions, and beeping an alarm at the time that the apparatus has been inadvertently remained in operation in spite of having the cooling system working at maximum.

Control and regulation automatic systems for inner temperature produced by the light bulbs and components are designed in printed circuits, with their respective cooling fans, for optical fiber light housing and d'Arsonval system housing.

Basic electronic components in optical fiber light housing are basically: a high voltage transformer, a ballast, a 6/12-volt, 5/10-amp high amperage low voltage transformer, two Xenon light bulbs (one for use and one spare), two metal halide (halogen) light bulbs (one for use and one spare), a regulated mini-motor for variable linearity filter displacement, potentiometers, integrated circuits and voltage regulators.

Basic electronic components in d'Arsonval light housing comprise: a Ruhmkorff induction coil, two pairs of lighters, capacitors (Leyden bottles) from 0.1 to 0.5 microfarads at a voltage between 3000-15000 volts, a d'Arsonval coil and Oudin resonator for a single-end plug connected to the Finch Strong vacuum glass tube in the desired color; special wiring and shielding to prevent interference. It is worth to mention specially that this d'Arsonval system will not be ever used in people with pacemakers.

III.—Optical Assembly.

1.—Lighting Step

The set in the head comprises two metal halide (halogen) light bulbs (one for use and one spare) located in a vertical direction parallel to the collecting lens, with a light bulb positioning mechanism which allows distance adjustment in two axes until the highest light intensity point is obtained, meeting the features of the so-called Kohler illumination microscopy.

The light emitted from the light bulb filament passes through the collecting lens, concentrating the light beam, which is reflected at 90 degrees by a mirror arranged for this purpose at 45 degrees in the light path axis.

It is important to emphasize that this invention consists of episcopic illumination, based on the illumination standards applicable to optics and microscopy, including Kohler illumination which allows the use of light energy with less expense and less heat emission.

1.—Light is emitted by an infinity-focused light source, passing through a positive or converging lens, deflecting the light beams and concentrating them in a focal plane such that a smaller diameter inverted image is provided.

2.—When using two converging lenses, and the second "front lens" lens focuses the image projected by the first "collecting" lens, the light source filament image passes without being seen in the focus focal plane, in this case the cervix; in other words, the focus image is a coiled filament and this image is unnoticed. The filament is not seen, but its energy can be used optimally as its beams in the second focal plane cross in parallel opposite to the projected image of the first converging lens. This is the Kohler principle.

The first lens image is projected onto the focal plane surface in this case, the cervix. Smooth and colorless as the glass, this is seen as a uniform light field. In the light of above, this illumination system was selected in our stereocolposcope. Our next step is:

2.—Excitation Step:

A variable linear filter has been chosen which may be adjusted to the selected working light frequency for exciting the desired compound, being called a head excitation filter, selecting a single wavelength, as in the case of our stereocolposcope. Another excitation filter has been similarly assembled in the optical fiber light housing, called the optical fiber housing excitation filter. The excitation color choice for the intended color in the d'Arsonval housing should be by selecting the vacuum glass tube corresponding to this emission.

The following describes the fluorophore, fluorescent protein, photodynamic therapy marker or fluorescent dye excitation in our system.

Firstly, that is applied at the cervix by a suitable technique, and absorbed by the infected tissue cells or in the lesions caused by human papillomavirus. The selected light beam is introduced on the cell tissue compound, thereby the light energy is absorbed in the tissues, and then emits light at a different light wavelength than that irradiated. The physical phenomenon of fluorescence thus arises: what is been looking for in the tissue fluoresces. The light energy irradiated by the excitation filter is absorbed by the compound atoms, exciting their electrons, changing spins, causing photon emission. The photon is produced when an electron changes its spin, photons with a wavelength other than that originally irradiated in cells and tissues (Stokes-Adams principle).

The above described reactions in photodynamic therapy application are also present.

3.—Suppression Step.

The light and image emitted by the irradiated compound is collected by the front lens and in parallel (one beam for each eye) is transmitted to the variable linearity suppression filters where the light frequency emitted from the compound is selected, modulating and matching with diaphragms of contrast and depth of field located inside the head optical system. Parallel image then passes through a assembled lens set (first eyepieces) in the Galileo drum to choose the desired amplification, sending the image to the Porro prisms which invert the image to be analyzed by the lenses by direct view or observation, or this image is sent instead to each of the two high-definition television cameras located at each of the two visual axes, the image then passes to the three-dimensional vision video system DLP (digital light processing) HDTV (High definition television) and this image is seen in the monitor by using three-dimensional active lenses.

The three-dimensional stereoscopic systems functions in this stereocolposcope at an angle between the two visual axes arranged between 7 to 12 degrees of opening.

Figure 1:
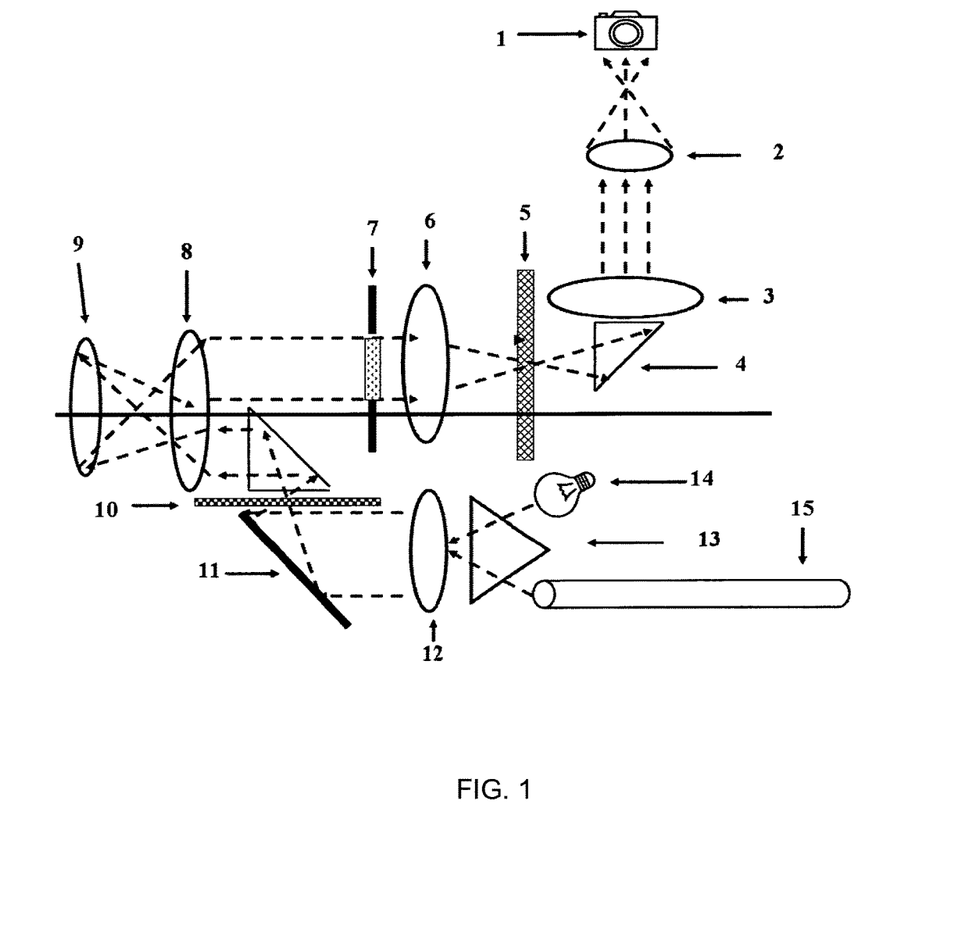
FIG. 1 shows schematically the optical system used in the stereocolposcope head in a single and easy way.

Description of FIG. 1: The number 1 indicates the image output where the video cameras or viewer's eyes are positioned, 2 and 3 numbers refer to the eyepiece lens which comprises image upper and receiving lenses, number 4 indicates inverting image prisms in order to view the images in the proper position (these are called Porro prisms). Number 5 indicates where the variable linearity barrier or suppressor filter is placed which is exactly at the light beam intersection which, as stated in the description, is for selecting the desired light spectrum that is emitted by the compound under study; this filter should slide through its axial axis thus choosing the desired frequency. Number 6 shows the interchangeable lens for choosing desired magnifications. Number 7 indicates the place for the contrast and depth of field diaphragm. Numbers 8 and 9 are the shooting lenses, front lens and second shooting lens and so on, these lenses are further used in the stereocolposcope as subject's illuminating light capacitor. Number 10 is the variable linearity excitation filter located where light beams coming from the illuminator converge. In order to choose the required wavelength for exciting the compound which will emit luminescence, the illuminator should only travel its longitudinal axis to select the desired frequency; this is also used in photodynamic therapy application using any drug intended for this purpose. Number 11 is a mirror providing the required focal length for the light emitted by the illuminator which is projected by the condenser collection lens marked with number 12. Number 13 is a prism selector to choose the required illumination pathway which may be emitted by halogen bulbs mounted on head 14 or that originating from the optical fiber 15 housing through the distal part thereof.

Figure 2:
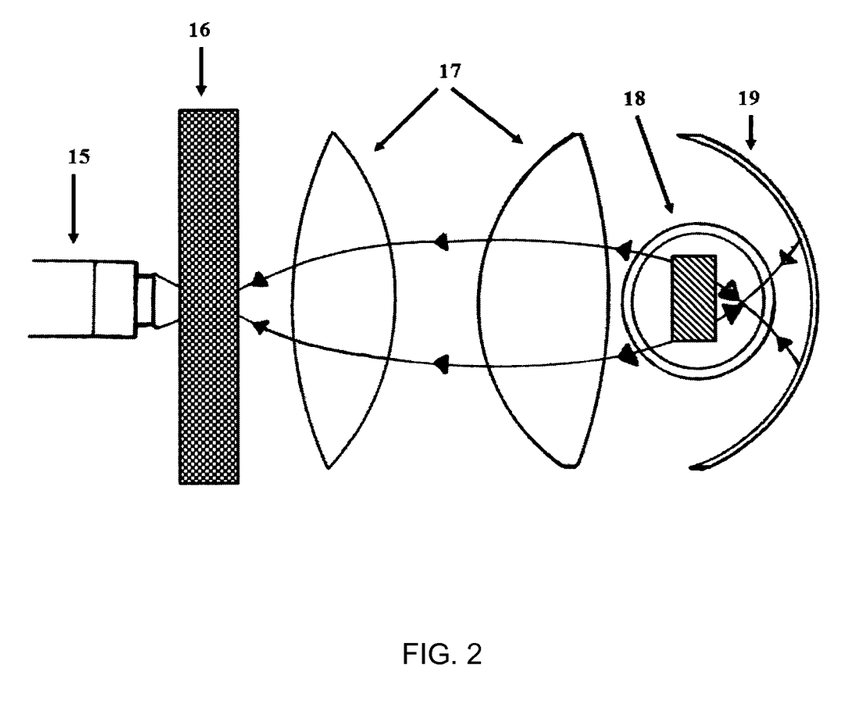
FIG. 2 shows the excitation variable linearity suppressor filter assembly used in the optical fiber light housing.

Description of FIG. 2: When the function is chosen from the optical fiber light housing, the head mounted excitation filter should be previously left out of the light beam axis in order to manipulate the light frequencies from the housing. Optical fiber 15 in its proximal housing portion is mounted on a special connector cylinder for this purpose; the variable linearity excitation filter is just located ahead being also slid for photodynamic therapy working excitation frequency choice, this filter is indicated by the number 16 in the drawing, high-power light source collecting converging lenses are indicated by the number 17. Number 18 indicates the xenon or high-power light irradiating lamp. A concave mirror 19 lies backwards to concentrate the light emitted by the lamp from its rear part, condensing and sending it to the front to take full advantage of the emitted energy.

Examples for the Use of a Two-Way Photodynamic Therapy Stereocolposcope.

The examples shown below are non-restrictive and non-limiting examples in the use of the apparatus when performed in practice, since as previously disclosed, this instrument is designed for multiple current and future applications in the medical field.

The use of the two-way photodynamic therapy stereocolposcope may be also useful, prior to introducing the following examples, as common stereocolposcopes with the usual technique of acetic acid test and iodine solution application, and the introduction of green filter for observing the capillary bed in the cervical-vaginal mucosal tissue.

Example 1. Diagnosis for Human Papillomavirus Lesions Using a Fluorochrome: Fluorescein Clinical Method.

The fluorescein isothiocyanate (FITC) fluorochrome was used in this case for several reasons:

This is widely used by ophthalmologists in fluoroangiographies (retina), and in local solution to see the corneal lesions. They use it with a lamp called "Actinic Lamp", which has a cobalt filter and the emission spectrum is blue. This lamp used by them has no suppresor filters, we have chosen this fluorochrome since it has no adverse or toxic effects in humans.

Procedure:

Place the patient comfortably in lithotomy position. Study duration is 15-20 minutes.

Introduce a plastic speculum to prevent unwanted reflections.
Locate the cervix.
Take vaginal pH (acidity or alkalinity): HPV infection often coexists with other bacterial or parasitic diseases so that the pH is alkaline.
Take samples from endocervix with cervical brush.
Take samples of ectocervix with Ayre spatula.
Prepare evenly tissue slide samples for laboratory, just to confirm our diagnosis, when required.
Apply 5% acetic acid to the cervix for a minute. This acidic solution has two functions, firstly a cell bleach in cervical intraepithelial neoplasm and secondly, a coupler for fluorochrome (FITC) application with cells.
Perform a routine colposcopic technique.
Insert the green filter to see vascular changes.
Make three-dimensional video-photographic records for comparison.
Apply evenly FITC (fluorescein isothiocyanate) to the cervix for a minute.
Select the frequency in the variable linearity excitation filter in a range of 488 nanometers (blue).
Select the frequency in variable linearity suppressor filters in a range of 520 nm (yellow).
Make direct observation or make video-photographic records with three-dimensional cameras mounted on the head.
When a patient is positive to fluorescein test, the image of the lesion will be seen in bright green color on a black background, if the patient were negative the black background would be without green image.

Example 2. Photodynamic Diagnosis (PPD) for Human Papillomavirus Lesions Using a Photosensitizing Agent, 5-Aminolevulinic Acid (ALA)

Clinical Method.
Procedure:
Place the patient comfortably in lithotomy position.
Introduce a vaginal speculum.
Locate the cervix.
Clean the cervix and vaginal walls with normal saline.
Apply the cream with the photosensitizer.
Putting the patient at rest for 2 hours.
Repeat the first three steps again.
Select the frequency in the head variable linearity excitation filter to a range of 405 nanometers (blue-violet).
Select the variable linearity suppressor filters at a range of 635 nanometers (red).
Make direct observation or make video-photographic records with three-dimensional cameras mounted on the head.
When a patient is positive to photodynamic diagnosis (PPD), the lesion image is seen in bright red on a black background, if the patient is negative the black background is simply seen without red image.

Example 3. Photodynamic Therapy (PPT) Application for Human Papillomavirus Lesions Using 5-Aminolevulinic Acid (ALA) Photosensitizing Agent Clinical Method.
This application is performed depending on status, clinical judgment and light irradiation required power in three modes.

Procedure 1:
Place the patient comfortably in lithotomy position.
Introduce a vaginal speculum.
Locate the cervix.
Clean the cervix and vaginal walls with normal saline.
Apply the cream with the photosensitizer.
Put the patient at rest for 4 hours.
Repeat the first three steps back.
Select the frequency in the head variable linearity excitation filter at a range of 685 nanometers (red).
Depending on the lesion, irradiate it by keeping the stereocolposcope focus distance for the necessary time.
This procedure is recommended for small lesions.

Procedure 2:
Place the patient comfortably in lithotomy position.
Introduce a vaginal speculum.
Locate the cervix.
Clean the cervix and vaginal walls with normal saline.
Apply the cream with the photosensitizer.
Put the patient at rest for 4 hours.
Repeat the first three steps back.
Select the frequency of the optical fiber housing variable linearity excitation filter in a range of 685 nanometers (red).
Place the optical fiber cable distal end into the adapter located in the head.
Depending on the lesion, irradiate it by keeping the stereocolposcope focus distance for the necessary time.
This procedure is recommended for moderate and severe lesions.

Procedure 3:
Place the patient comfortably in lithotomy position.
Introduce a vaginal speculum.
Locate the cervix.
Clean the cervix and vaginal walls with normal saline.
Apply the cream with the photosensitizer.
Put the patient at rest for 4 hours.
Repeat the first three steps back.
Turn d'Arsonval housing and select the applicator, in this case a Finch Strong glass vacuum tube with red emission color (vaginal type Finch Strong glass vacuum tube)
Place the applicator distal end on the cervix.
Depending on the lesion, irradiate it by keeping the stereocolposcope focus distance for the necessary time.
This procedure is recommended for moderate and severe lesions.

Example 4. Electrotherapy Application in Infections by Vaginitis and Vaginosis Producing Bacteria Clinical Method.
Procedure:
Place the patient comfortably in lithotomy position. The duration of treatment application is 15-20 minutes.
Introduce a plastic speculum (electrically isolated).
Locate the cervix.
Take vaginal pH (acidity or alkalinity): bacterial or parasitic diseases cause variation in pH and usually alkalinize it.
Take samples from endocervix with cervical brush.
Take samples of ectocervix with Ayre spatula.
Prepare smooth tissue slide samples and culture tubes to be sent to the laboratory, when required.
Clean the female genital tract with 5% acetic acid
Perform a routine colposcopic technique.
Introduce the green filter to see vascular changes.

Make video-photographic three dimensional records.

Turn d'Arsonval housing and choose the applicator, in this case a Finch Strong glass vacuum tube with violet emission color (vaginal type Finch Strong glass vacuum tube)

Place the applicator distal end on the cervix.

Depending on infection nature, irradiate manually the genital tract with the applicator like an electrofulguration, in order to produce a large amount of ozone on the infected tissue surface, keeping the stereocolposcope focus distance and watching the applicator as needed.

The invention claimed is:

1. A system for diagnosis and treatment of female genital tract diseases comprising:
   a stereocolposcope for three-dimensional observation including a head with a lighting system, the lighting system including:
      a first light source;
      collecting lenses for concentrating light beam;
      a variable linear type excitation filter system configured to choose any light frequency range to generate a light beam to send to any compound located at the female genital tract covering a range from 400 nanometers to 1080 nanometers, a light beam band being selectable every 20 nanometers;
      two variable linear suppressors or barrier filters, one for each observation optical axis for adjusting emission beams issued from a compound to be reacted in a dyed female genital tract with a light spectrum from 400 to 700 nanometers; and
      two diaphragms, one on each optical axis with a manual opening controller to contrast an image and watching a depth of field; and
   a light source housing with a focusable optical system and directed to an optical fiber including:
      a second light source,
      collecting converging lenses; and
      a variable linearity filter configured to choose any light frequency range to generate a light beam to send to any compound located at the female genital tract covering a range from 400 nanometers to 700 nanometers, the light beam band being selectable every 20 nanometers,
   wherein the stereocolposcope is configured to perform two way photodynamic therapy by manual selection of one light source that is activated based on a desired treatment.

2. The system according to claim 1, wherein the optical fiber is a medical grade optical fiber or an optical fiber made of ethylene and propylene fluorinate (FEP) resin.

3. The system according to claim 1, further comprising a third light source housing with d'Arsonval system or violet ray, consisting of a Ruhmkorff induction coil, Leiden bottles or capacitors, lighters, a high frequency d'Arsonval coil, Oudin resonator which radio frequency emission end cable thereof is connected to an applicator's electrode, which is Strong Finch vacuum glass tube; and wherein the vacuum glass tube is of vaginal type with emission in different colors spanning a visible light spectrum.

4. The system according to claim 1, wherein the lighting system consists of episcopic illumination, based on Kohler principle.

5. The system according to claim 1, wherein the three-dimensional observation is by direct observation through an eyepiece or by two high resolution video cameras placed on said head, each camera being placed in each visual axis.

6. The system according to claim 1, wherein the three-dimensional observation is by a three-dimensional video vision system including DLP (digital light processing) HDTV (high definition television) with use of three-dimensional active lenses.

7. The system according to claim 1, further comprising a high-amperage power line isolator transformer.

8. A system comprising:
   a stereocolposcope for three-dimensional observation including a head with a lighting system, the lighting system including:
      a first light source;
      collecting lenses for concentrating light beam;
      a variable linear type excitation filter system that is configured to (i) select a first light frequency from a first light frequency range of 400 nanometers to 108 nanometers and (ii) provide a first light beam to a compound of a female genital tract based on the first light frequency;
      two variable linear suppressor filters that are each located on a observational axis and are each configured to adjust at least one emission beam transmitted from the compound of the female genital tract that reacts with a dyed female genital tract, wherein the at least one emission beam is converted to a second light frequency selected from a second light frequency range of 400 nanometers to 700 nanometers; and
      two diaphragms that are each located on an optical axis with a manual aperture controller, wherein the two diaphragms are configured to contrast an image and control a depth of field; and
   a light source housing with a focusable optical system coupled to, using an optical fiber, at least one of the compound of the female genital tract and a drug within the female genital tract, wherein the focusable optical system includes:
      a second light source,
      collecting converging lenses, and
      a variable linearity filter that is configured to (i) select a third light frequency from a third light frequency range of 400 nanometers to 700 nanometers and (ii) provide a third light beam for photodynamic therapy to at least one of the compound of the female genital tract and the drug within the female genital tract based on the third light frequency,
   wherein the stereocolposcope is configured to perform two way photodynamic therapy by manual selection of one light source that is activated based on a desired treatment.

* * * * *